(12) United States Patent
Boucher

(10) Patent No.: US 7,010,431 B2
(45) Date of Patent: Mar. 7, 2006

(54) METHOD FOR EFFECTING COMPUTER IMPLEMENTED DECISION-SUPPORT IN THE SELECTION OF THE DRUG THERAPY OF PATIENTS HAVING A VIRAL DISEASE

(75) Inventor: Charles Achim Bernard Boucher, Utrecht (NL)

(73) Assignee: F. Hoffman-LaRoche Ltd., (NL)

( * ) Notice: Subject to any disclaimer, the term of this patent is extended or adjusted under 35 U.S.C. 154(b) by 237 days.

(21) Appl. No.: 10/058,622

(22) Filed: Jan. 28, 2002

(65) Prior Publication Data

US 2002/0107705 A1    Aug. 8, 2002

Related U.S. Application Data

(63) Continuation of application No. 09/902,624, filed on Jul. 12, 2001, now abandoned.

(30) Foreign Application Priority Data

Jul. 13, 2000   (EP)   ................................. 00202482

(51) Int. Cl.
*C12Q 1/68* (2006.01)
*G01N 33/48* (2006.01)
*G06F 17/30* (2006.01)

(52) U.S. Cl. ................................. 702/19; 435/6; 707/1
(58) Field of Classification Search ................. 702/19; 435/6; 436/6; 707/1
See application file for complete search history.

(56) References Cited

U.S. PATENT DOCUMENTS 5,985,559 A    11/1999   Brown ........................... 435/6

OTHER PUBLICATIONS

Dunn et al. Isolation of efficient antivirals: genetic suppressor elements against HIV-1. Gene Therapy. Jan. 1999, vol. 6 No. 1, pp. 130-137.*
Lewis et al. Zidovudine Induces Molecular, Biochemical, and Ultrastructural Changes in Rat Skeletal Muscle Mitochondria. Apr. 1992, vol. 89, pp. 1354-1360.*
Lathrop et al., "Knowledge-based Avoidance of Drug-Resistant HIV Mutants", *American Association of Artificial Intelligence*, 1998, pp. 1071-1078.
Pazzani et al., "CTSHIV.: A Knowledge-Based System for the Management of HIV-infected Patients", *Proceedings: Intelligent Information Systems*, IIS'97 (CAT. No. 97TB100201), 1997 pp. 7-13.
Lathrop et al., "Knowledge-based Avoidance of Drug-Resistant HIV Mutants", *American Association for Artificial Intelligence*, Spring 1999, pp. 13-25.
Lathrop et al., "Combinatorial Optimization in Rapidly Mutating Drug-Resistant Viruses", *Journal of Combinatorial Optimization*, 1999, pp. 301-320.

* cited by examiner

*Primary Examiner*—Ardin H. Marschel
*Assistant Examiner*—Shubo (Joe) Zhou
(74) *Attorney, Agent, or Firm*—Knoble Yoshida & Dunleavy, LLC

(57) ABSTRACT

A method is described for effecting computer-implemented decision-support in the selection of a drug therapy of patients having a viral disease. A rules database is provided and patient data is entered including genotype data on the viral genome of the viral disease. The rules database comprises a number of associated rules for each available drug for treatment of the viral disease. Each rule indicates the suitability of the drug for treatment of a specific viral genotype. The patient data is entered into the rules database, the database providing an output of drugs suitable for therapy. The drugs suitable for therapy are displayed in a ranking in accordance with their suitability indication, for selection.

43 Claims, 2 Drawing Sheets

Figure 1:
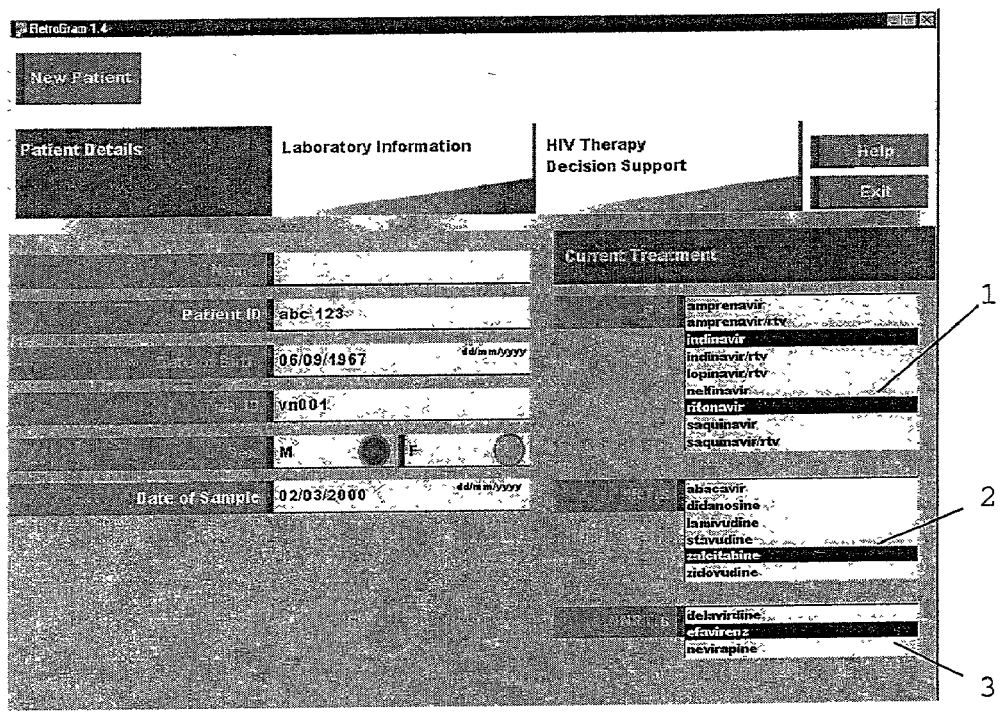

METHOD FOR EFFECTING COMPUTER IMPLEMENTED DECISION-SUPPORT IN THE SELECTION OF THE DRUG THERAPY OF PATIENTS HAVING A VIRAL DISEASE

Continuation of prior application Ser. No. 09/902,624 filed Jul. 12, 2001 now abandoned.

The present invention relates to a method for effecting computer-implemented decision-support in selection of a drug therapy of patients having a viral disease.

WO 9727480 discloses a method for managing HIV chemotherapy of patients who are HIV positive based on the genotypic drug sensitivity of human HIV strains. According to this known method a cell line is transfected, the transfected cells are cultured and the sensitivity to an inhibitor is assessed to obtain a data set on the virus sensitivity. The optimum inhibitors, i.e. drug(s) for chemotherapy, is/are selected on the basis of a graphical representation of the data obtained in this manner. This known method requires extensive laboratory work and is time consuming.

The invention aims to provide an improved method of the above-mentioned type.

According to the invention a method for effecting computer implemented decision-support in selection of a drug therapy of patients having a viral disease, comprises providing a rules database, providing an input of patient data including genotype data on the viral genome of the viral disease, wherein the rules database comprises a number of associated rules for each available drug for treatment of the viral disease, each rule indicating the suitability of the drug for treatment of a patient infected with a specific viral genotype, entering the patient data into the rules database, the database providing an output of drugs suitable for therapy, and displaying the drugs suitable for therapy in a ranking in accordance with their suitability indication, for selection.

In this manner a tool is obtained by means of which a physician is provided with a clear and concise overview of the individual drugs and information relevant to each of them. He can take this information into account when deciding on a drug therapy for a particular patient. Extensive laboratory tests to determine the phenotypic sensitivity as in the prior art method are not required. The method of the invention thereby reduces the time period needed to obtain data for selecting a suitable drug therapy from 2–3 weeks to 2 days. Any new information on drug resistance of specific genotypes can be introduced into the rules database in an easy manner.

In the preferred embodiment of the invention, the suitability indication of the rules is based on at least a first value indicating the resistance level of the genotype for the drug when present at a certain drug level in a patient. Thus, the selection of the most suitable drugs is further refined. Rather than judging whether a drug is suitable solely on the basis of a viral genotype, the suitability is based on the effect the drug would have at a certain drug level in a patient with that viral genotype, usually the drug level that is most likely to occur.

In a preferred embodiment that enhances the embodiment just described, the first value is a function of the drug level, and an expected drug level in the patient is further provided and entered in the database. Thus, the method can determine the suitability of drugs in a way that is even more specific to the particular patient, because the expectation will usually be based on data characterizing that particular patient, for example measurements of drug levels in a blood sample taken from the patient.

The invention will now be further explained by reference to the drawings.

FIGS. 1–4 show different displays presented during use of an embodiment of the method of the invention.

In the following description an embodiment of the method of the invention will be described as applied in determining a drug therapy or regimen of an HIV infected patient. However, the method of the invention can also be used in determining drug therapies for treatment of patients having other viral diseases, for example hepatitis B or hepatitis C.

The method is implemented as a computer application program that can be run on any suitable PC. According to the method a rules database is provided, wherein the rules database comprises for each presently available drug for treatment of HIV a number of associated rules. In an embodiment of the method described by way of example only, fourteen drugs are included in the database, comprising six nucleoside reverse transcriptase inhibitors, three non-nucleoside reverse transcriptase inhibitors and five protease inhibitors. Further, four protease combinations are present, the so-called boosted protease inhibitors regimens.

As known, the information content of an HIV is contained in a set of genes encoded in its genome. The genome governs the production of proteins, important in the virus life cycle. A protein is a sequence of amino acids, with each amino acid being one of twenty different varieties. In the embodiment described, the proteins targeted by the drugs included in the rules database are reverse transcriptase (RT) and protease (P). It will be understood however that generally the rules database may comprise rules regarding other proteins and drugs targeted at such proteins, Reverse transcriptase and protease are mentioned by way of example only and the invention is not restricted to rules and drugs targeted at these proteins only. When gene mutations occur, different amino acids may be substituted in these proteins. Research has shown that certain substitutions cause resistance to certain drugs. The knowledge included in the rules database is obtained from scientific articles and the like. More specifically, the rules of the database are based on the international (peer-received) scientific literature on HIV-resistance. The rules are updated frequently and the new rules reflect the latest publications on this subject.

To guarantee the quality of the rules used, the updated rules are first built into a prototype of the method described. A large number of independent international clinical and virological experts evaluate the new prototype running panels of clinical samples. The feedback of all experts is then presented to a core-committee of ten academic experts who weigh up these contributions to determine the final rules.

All pharmaceutical companies producing anti-retroviral drugs receive the prototype and evaluate the performance for their drugs. The comments of the companies need to be supported by scientific and/or clinical evidence, and are also presented to the core-committee. The core-committee determines the final set of rules that are contained in the release version of the software in which the method described is implemented.

A substitution is generally represented by a number for the position of the substitution in the gene and a letter for the amino acid. The protease portion of the gene has 99 positions and the reverse transcriptase portion of the gene has at least 500 positions. At each position one of twenty different amino acids may occur, wherein however the number of substitutions known to occur at each gene position is small. Examples of the format to indicate substitutions are 70R, 151M and 215Y. It is noted that the HIV reference genome used in this description is known as NL4-3.

As will be described hereinafter, genomic information is entered and the method identifies different categories of substitutions, the categories being relevant, natural or unreported. Relevant substitutions are those substitutions that are taken into account by the method when using the rules database to assess the suitability level of the drugs. Natural substitutions are those substitutions that are known to occur, but which are not known to affect drug resistance. Finally, unreported substitutions are substitutions which are currently not known to the system, and whose effects on drug resistance are also unknown.

For each substitution or combination of substitutions known to affect drug resistance, a set of three values is assigned to each drug giving information about the effects of substitutions.

The first value is indicated as resistance level providing information on how much resistance is conferred on this drug by this substitution. The resistance level is represented on a scale from 0 (low resistance) to 3 (high resistance).

A major advantage of the invention is that the resistance level is not only related to the particular substitution, but also to a certain drug level in a patient. Two parameters thus determine the suitability level, namely drug resistance and drug activity. The drug level, simply put, the concentration of the drug in a patient's body, depends on the dose taken by the patient and the patient's metabolism.

In its most basic form, the certain drug level on which the resistance level is related is the drug level found statistically to occur most often in patients given the recommended dose of the drug.

In a more advanced version of the invention, the first value is stored in the database as a function of the drug level. This allows a differentiation according to patient, since the drug level resulting from a certain drug dosage can vary from patient to patient. Information entered concerning the drug level expected for a patient can then be used to determine the suitability of a drug. The information can be based on a patient profile and statistical data. Preferably, however, it is based on measurements of a drug level occurring in a patient, obtained, for example, by analysis of blood or tissue samples taken from the patient.

The second value assigned to each drug is indicated as confidence level Indicating how much support there is for this result in the scientific literature. A confidence level has one of the three following levels:
 (1) suggestive evidence,
 (2) proven in vitro,
 (3) proven in vivo Finally the third value assigned to each drug is indicated as suitability level and this suitability level is based on combining and weighing the resistance level, the drug level, the confidence level and clinical experience This suitability level indicates the suitability of the drug for use with the given substitutions of the HIV of a specific patient. Suitability levels range as follows:
 0 or A Can be used
 1 or B Consider use if level A drug not available
 2 or C Consider use if drug at level A or B not available
 3 or D Consider use if drug at level A, B or C not available
 4 or U Not enough data is available to make any comment For rules with a suitability level U, the resistance and confidence levels are not normally given.

The clinical experience can mean experience provided by experts, or it can comprise the outcome of clinical studies relating the presence of substitutions at start of therapy directly to clinical or virological outcome.

In the rules database, each rule indicates the resistance, confidence, and suitability levels, except for the suitability level U as indicated above, There are separate rules for P substitutions, which affect PI drugs, and RT substitutions, which affect NRTI and NNRTI drugs. Where a substitution appears in a rule without a letter, it is assumed to represent all the relevant substitutions. Some rules reference single substitutions, whereas others specify combinations of substitutions. Some example rules for protease substitutions are as follows:

| substitution | drug | resistance @ level | confidence | suitability |
| --- | --- | --- | --- | --- |
| 48 V | IND | 0 | 100 | 2 | 1 |
| 48 V | IND (+RTV) | 0 | 1000 | 2 | 1 |
| 48 V | IND (+RTV) | 1 | 100 | 2 | 2 |
| 82A/F/T/S | IND | 1 | 100 | 2 | 1 |
| 84 + 90 + 46 | NFV | 3 | 100 | 3 | 3 |
| 48 V | FTV | 1 | 100 | 2 | 2 |
| 90M/I | AMP | 1 | 10000 | 2 | 2 |

It is noted that the substitution 82A/F/T/S should be read as any of 82A, 82F, 82T or 82S, whereas the substitution 84+90+46 should be read as a relevant substitution at 84 and a relevant substitution at 90 and a relevant substitution at 46.

Some example rules for RT substitutions are as follows:

| substitution | drug | resistance @ level | confidence | suitability |
| --- | --- | --- | --- | --- |
| 215Y/F + 41 | ZDV | 3 | 100 | 3 | 3 |
| 236 | NVP | 0 | 100 | 2 | 0 |
| three of (41, 67, 70, 210, 215, 219) | D4T | 1 | 100 | 1 | 1 |
| 184 + two of (41, 67, 70, 210, 215, 219) | ABC | 2 | 10000 | 2 | 3 |
| 69SS + 215 | 3TC | 2 | 100 | 2 | 2 |
| 179D | DLV | — | 100 | — | — |

In applying the rules database, for each PI or NRTI drug, where one of more rules apply, the suitability level is the maximum of all levels derived. For each NNRTI drug, where more than one rule applies, the suitability level is the sum of all levels derived, up to a maximum of 3.

As shown in the second and third rows of the first of the above-provided tables, further rules can be present, when the use of one drug affects the suitability of a drug. It has been found that certain drugs taken in combination with another drug are present at much higher drug levels in the patient, because the other drug affects the uptake of that certain drug by the patient. Accordingly, the first value in the rule for that drug, when taken in combination, will be based on a different drug level.

The presence of another drug can also influence the value of the resistance level to another drug, through the selection of certain substitutions, which influence the resistance to the other drug. This leads to a different first value in the rule for that drug when taken in combination with the other drug, than is comprised in the rule for the drug when taken on its own.

In using the rules database for determining the drug therapy of a patient, patient data should be provided as input to the rules database. For this purpose, the program implementing the method allows to enter patient details using a display as shown in FIG. 1. Patient data to be entered includes patient's name, a patient's identifier and the date of the patient's blood sample from which the laboratory results were obtained. Further it is possible to enter data on the current treatment of the patient in three different fields, i.e. a PI drug field 1, a NRTI drug field 2 and a NNRTI drug field 3. The names of the available drugs are shown and clicking on a drug name in any of the three fields indicates that this drug is used in the current treatment of the patient. Clicking on a drug name again deselects that drug. Any number of drugs from each list may be selected.

Figure 2:
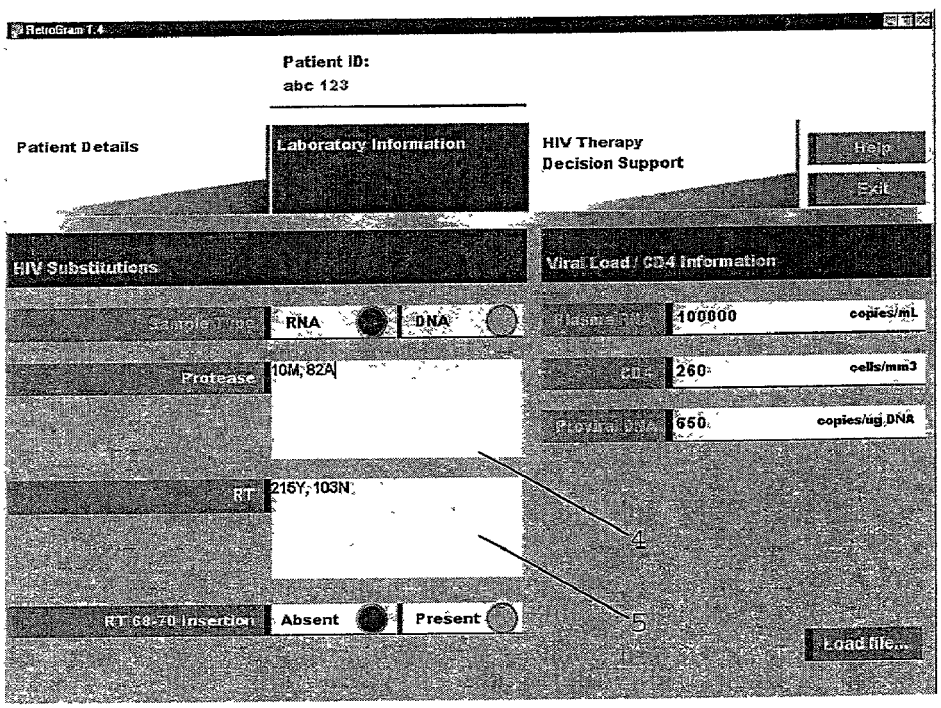

The laboratory results obtained from the blood sample of the patient can be entered by means of the display shown in FIG. 2. As shown in FIG. 2, the display includes a protease field 4 and a reverse transcriptase field 5. In these fields the P and RT substitutions are entered separately and this information is used by the rules database to provide information on the drugs to be used preferably for treatment of the patient.

Further data to be entered may comprise information on the viral load, the CD4 cell count, if known, and the clade classification. The clade classification can be selected from a drop-down menu. As an alternative, the genotype data entered in fields 4, 5, can be used by the method to identify the clade to which the virus in the patient belongs. The clade information can be used in selecting a drug therapy.

When the database comprises tables linking drug resistance values to drug levels, further data will be entered. Ideally, this will be the result of patient-specific drug level measurements, which are easily obtained during analysis of the blood sample taken from the patient, especially when the patient is already taking a drug. Alternatively relevant statistical data, like the patient's weight, can be used to provide an estimate of the likely drug level. If this is not possible, data from clinical trials on groups of patients could, for example be used to provide an expected drug level.

As an alternative for entering the genotype or substitution data manually in the fields 4, 5, this data can be read directly from an output file of the sequencer system used to determine the genotype data The sequencer output file is loaded by clicking on a button on the display of FIG. 2 labelled "Load file".

Figure 3:
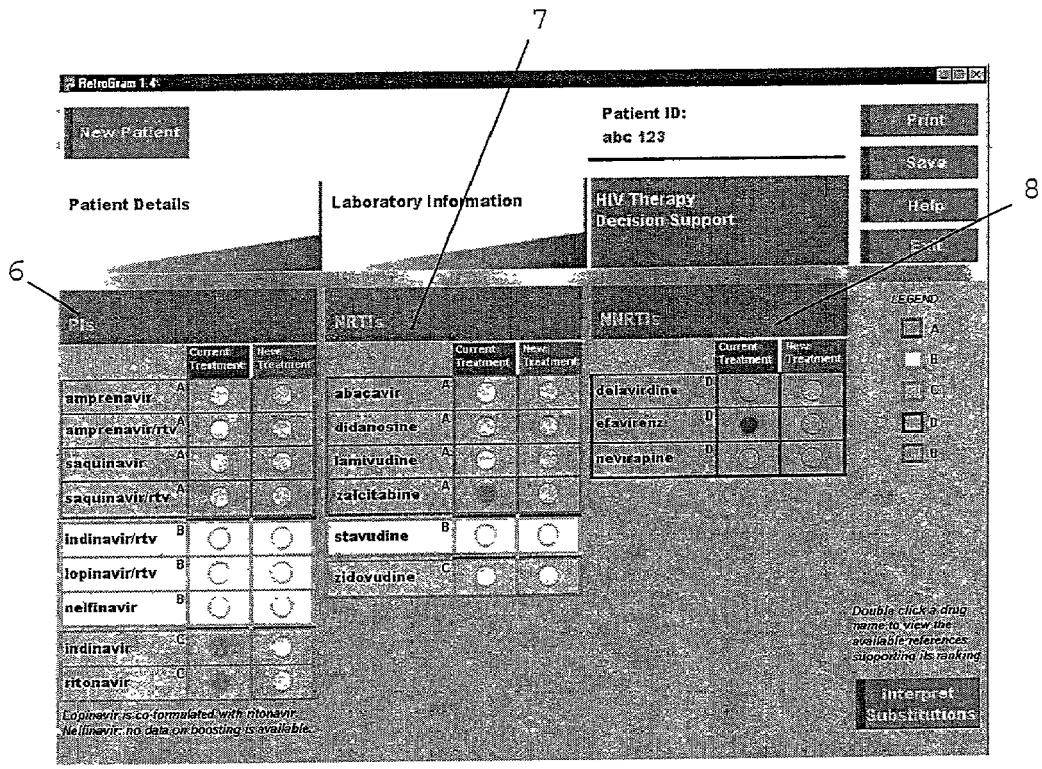

The P and RT substitutions data or more generally genotype data of the viral genome is used by the rules database to provide a drug ranking as shown for example in the display of FIG. 3. According to FIG. 3, the drugs are again divided into three separate groups, i.e. PI group 6, NRTI group 7 and NNRTI group 8. Within each group 6, 7, 8 the drugs are individually ranked depending on the substitution data entered, with the drugs least likely to be associated with clinical resistance in this patient appearing at the top of each list.

The preferred embodiment of the invention has the advantage that drug levels are used to refine the ranking. Where two drugs have equal suitability indications, the drug level is used to place them in the ranking. The drug to which resistance occurs at higher drug levels is placed above the drug to which resistance occurs at lower levels. In this way, the effect of another drug on the drug level can be taken into account when compiling the ranking. If a second drug leads to a higher level of a first drug, then the combination of the two is placed higher in the ranking.

As shown in FIG. 3, the drugs are ranked individually according to their suitability. Where certain drugs influence each other's suitability level, combinations of drugs are included in the ranking. This provides a concise overview to the physician using the invention. The physician can select drugs one at a time at his own discretion to devise a complete drug regimen for therapy. Only when one drug affects the suitability indication of another is the combination comprised in the ranking. The physician does not have to choose between a large group of combinations of drugs and can take into account any additional knowledge and experience of the drugs and the patient's reaction to them.

The ranking of the drugs can be emphasised by using different colours in the ranking. Other ways of emphasising the ranking are, of course, also conceivable, including flashing displays or the addition of symbols.

As shown in FIG. 3, each drug in the ranking lists 6, 7, 8 has two associated buttons, wherein the left-hand button is shown selected if the patient is already taking this drug as entered as current treatment in the display of FIG. 1. The right-hand button refers to a new treatment and may be selected or deselected by clicking and indicates whether this drug is being chosen as a new treatment for this patient.

The display of FIG. 3 can include a button "Continue On Regimen", wherein by clicking this button it is indicated to continue with the current treatment for the patient. This automatically highlights all the new treatment buttons to match the current treatment buttons.

The display of FIG. 3 has a further button "Interpret Substitutions", wherein by clicking this button the classification of the substitutions of the patient will be shown on the screen. The method classifies each substitution entered by the user in the display of FIG. 1 into one of the three above-mentioned categories.

Figure 4:
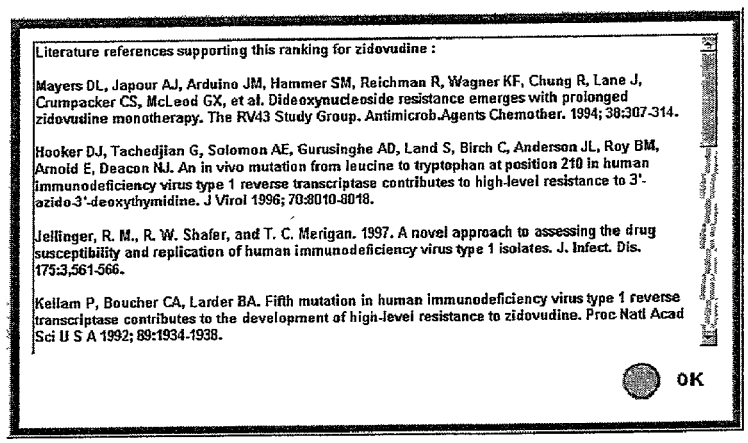

If the user is interested to obtain further information on the drug ranking, the user can obtain further information by double-clicking on any drug name in the ranking list. In this manner a list of available references from the scientific literature will be displayed supporting the particular ranking for that drug. An example of the display obtained is shown in FIG. 4.

As mentioned above the method can bemused by running a program implementing the method on a PC. The program can be distributed on any suitable program carrier or by downloading from the Internet. As an alternative the method can be implemented by running the program on a central computer which provides directly or through an intermediate server a web-site on the Internet. The web-site allows the use of the program. Access is possible by means of any known web browser. Of course any suitable restricted access by means of passwords and identifications can be implemented. This embodiment shows the advantage of an optimal control on updates of the program and rules database.

The method described shows the advantage that in a laboratory test only the genotype data need to be determined and extensive laboratory tests to determine resistance against drugs is avoided. Available evidence and the advice of an expert panel are combined in suitability level advice of available drugs. In this manner the user can determine a drug therapy in a very efficient manner so that treatment of a patient is not postponed unnecessarily. As soon as new reliable data becomes available, this data can be added to the rules database in the form of new rules.

The invention is not restricted to the above-described embodiment, which can be varied in a number of ways within the scope of the claims.

The invention claimed is:

1. Method for effecting computer implemented decision-support in selection of a drug therapy of patients having HIV, comprising using a rules database, providing an input of patient data including genotype data on the viral genome of the HIV, wherein the rules database comprises a number of associated rules for each available drug for treatment of the HIV, each rule indicating the suitability of the drug for treatment of a specific HIV viral genotype, entering the patient data into the rules database, the database providing an output of drugs suitable for therapy, and displaying the drugs suitable for therapy in a ranking in accordance with their suitability indication, for selection, wherein the suitability indication of the rules is based on at least a combination of a first value indicating the resistance level of the genotype for the drug and a second value indicating the confidence in the first value.

2. Method according to claim 1, wherein the suitability indication is based on at least a combination of the first and second values and clinical experience.

3. Method according to claim 2, wherein the clinical experience comprises the outcome of clinical studies relating the presence of substitutions at start of therapy directly to clinical or virological outcome.

4. Method according to claim 1, wherein the second value can indicate as confidence level suggestive evidence, proven in vitro or proven in vivo.

5. Method according to claim 1, wherein the suitability indication of the rules is based on at least a first value indicating the resistance level of the genotype for the drug when present at a certain drug level in a patient.

6. Method according to claim 5, wherein the first value is a function of the drug level, wherein an expected drug level in the patient is further provided and entered in the database.

7. Method according to claim 6, wherein the expected drug level is based on a patient-specific drug level measurement.

8. Method according to claim 5, wherein two or more drugs or combinations of drugs with equal suitability indication are ranked relative to one another according to the drug levels on which the rules for the drugs are based.

9. Method according to claim 1, wherein the database further comprises a rule for a drug available for treatment, the rule indicating the suitability of the drug for treatment of a specific HIV viral genotype when the drug is taken in combination with another drug, wherein the combination of the drugs is displayed in the ranking with the individual drugs according to the suitability indication for the combination.

10. Method according to claim 9, wherein the rule is based on the effect of the other drug on the level of the drug in a patient.

11. Method according to claim 1, wherein the rules database comprises rules for different protein substitutions.

12. Method according to claim 11, wherein the rules database comprises rules for (P) substitutions and reverse transcriptase (RT) substitutions.

13. Method according to claim 1, wherein the drugs available for therapy are displayed as output from the database in different categories in accordance with the type of drug activity.

14. Method according to claim 13, wherein the type of drug activity includes protease inhibitor, nucleoside RT inhibitor and non-nucleoside PT inhibitor.

15. Method according to claim 1, wherein the patient data input comprises the clade of the HIV virus, wherein the clade is used in the step of selecting a suitable drug therapy.

16. Method according to claim 15, wherein the entered genotype data is used to determine the clade of the HIV virus.

17. Method according to claim 1, wherein the patient data input comprises a drug therapy as current treatment, wherein in the display of the drugs it is indicated at each drug if the same is used in the current treatment.

18. Method according to claim 1, wherein a database of reference articles on one or more of the drugs available for treatment is provided, wherein a list of reference articles can be displayed by entering a request on a given drug, the list containing articles supporting the suitability of the drug for treatment of the HIV with the entered genotype data.

19. Method according to claim 1, wherein a classification of the genotype data of the HIV viral genome can be indicated, wherein the rules database is used to classify the genotype data at least as relevant or not to assessing the suitability level of the drugs.

20. Method according to claim 19, wherein the genotype data comprises data on substitutions in the HIV viral genome, wherein each substitution can be classified into three categories, wherein the first category indicates relevant to drug resistance, the second category indicates that the substitution is known, but not known to affect drug resistance, and the third category indicates that the substitution is not reported to have an effect on drug resistance.

21. Method according to claim 1, wherein the computer and database are accessible via a web-site.

22. A computer program device readable by a computer, comprising a computer program executable by the computer for effecting the computer to carry out the method of claim 1.

23. Computer program carrier, comprising a computer program in a format downloadable by a computer, comprising a computer program executable by the computer for effecting the computer to carry out the method of claim 1.

24. Method for effecting computer implemented decision-support in selection of a drug therapy of patients having HIV, comprising providing a rules database, providing an input of patient data including genotype data on the viral genome of the HIV, wherein the rules database comprises a number of associated rules for each available drug for treatment of the HIV, each rule indicating the suitability of the drug for treatment of a specific HIV viral genotype, entering the patient data into the rules database, the database providing an output of drugs suitable for therapy, and displaying the individual drugs suitable for therapy in a ranking in accordance with their suitability indication, for selection, wherein the database further comprises a rule for at least one certain drug available for treatment, the rule indicating the suitability of the certain drug for treatment of a specific HIV viral genotype when the drug is taken in combination with another drug, wherein only combinations of drugs are displayed in the ranking with the individual drugs according to the suitability indication for the combination where drugs in the combination influence each other's suitability indication.

25. Method according to claim 24, wherein the suitability indication of the rules is based on at least a combination of a first value indicating the resistance level of the genotype for the drug and a second value indicating the confidence in the first value.

26. Method according to claim 25, wherein the suitability indication is based on at least a combination of the first and second values and clinical experience.

27. Method according to claim 25, wherein the second value can indicate as confidence level suggestive evidence, proven in vitro or proven in vivo.

28. Method according to claim 24, wherein a rule indicating the suitability of the certain drug for treatment of a specific HIV viral genotype when the drug is taken in combination with another drug, is based on the effect of the other drug on the level of the drug in a patient.

29. A computer program device readable by a computer, comprising a computer program executable by the computer for effecting the computer to carry out the method of claim 24.

30. Computer program carrier, comprising a computer program in a format downloadable by a computer, comprising a computer program executable by the computer for effecting the computer to carry out the method of claim 24.

31. Method for effecting computer implemented decision-support in selection of a drug therapy of patients having HIV, comprising providing a rules database, providing an input of patient data including genotype data on the viral genome of the HIV, wherein the rules database comprises a number of associated rules for each available drug for treatment of the HIV, each rule indicating the suitability of the drug for treatment of a specific HIV viral genotype, entering the patient data into the rules database, the database providing an output of drugs suitable for therapy, and displaying the drugs suitable for therapy in a ranking in accordance with their suitability indication, for selection, wherein the suitability indication of the rules is based on at least a first value indicating the resistance level of the genotype for the drug when present at a certain drug level in a patient.

32. Method according to claim 31, wherein the first value is a function of the drug level, wherein an expected drug level in the patient is further provided and entered in the database.

33. Method according to claim 32, wherein the expected drug level is based on a patient-specific drug level measurement.

34. Method according to claim 31, wherein two or more drugs or combinations of drugs with equal suitability indication are ranked relative to one another according to the drug levels on which the rules for the drugs are based.

35. Method according to claim 31, wherein the database further comprises a rule for a drug available for treatment, the rule indicating the suitability of the drug for treatment of a specific HIV viral genotype when the drug is taken in combination with another drug, wherein the combination of the drugs is displayed in the ranking with the individual drugs according to the suitability indication for the combination.

36. Method according to claim 35, wherein the rule is based on the effect of the other drug on the level of the drug in a patient.

37. Method according to claim 31, wherein the patient data input comprises a drug therapy as current treatment, wherein in the display of the drugs it is indicated at each drug if the same is used in the current treatment.

38. A computer program device readable by a computer, comprising a computer program executable by the computer for effecting the computer to carry out the method of claim 31.

39. Computer program carrier, comprising a computer program in a format downloadable by a computer, comprising a computer program executable by the computer for effecting the computer to carry out the method of claim 31.

40. Method for effecting computer implemented decision-support in selection of a drug therapy of patients having HIV, comprising providing a rules database, providing an input of patient data including genotype data on the viral genome of the HIV, wherein the rules database comprises a number of associated rules for each available drug for treatment of the HIV, each rule indicating the suitability of the drug for treatment of a specific HIV viral genotype, entering the patient data into the rules database, the database providing an output of drugs suitable for therapy, and displaying the drugs suitable for therapy in a ranking in accordance with their suitability indication, for selection, wherein the clade is used in the step of selecting a suitable drug therapy.

41. Method according to claim 40, wherein the entered genotype data is used to determine the clade of the HIV virus.

42. A computer program device readable by a computer, comprising a computer program executable by the computer for effecting the computer to carry out the method of claim 40.

43. Computer program carrier, comprising a computer program in a format downloadable by a computer, comprising a computer program executable by the computer for effecting the computer to carry out the method of claim 40.

* * * * *